US012770736B2

(12) United States Patent
Britto Mattos Lima et al.

(10) Patent No.: US 12,770,736 B2
(45) Date of Patent: Oct. 20, 2026

(54) TRAINING AND IMPLEMENTING A FOUR-DIMENSIONAL DATA OBJECT RECOMMENDATION MODEL

(71) Applicant: Microsoft Technology Licensing, LLC, Redmond, WA (US)

(72) Inventors: Andréa Britto Mattos Lima, Sao Paulo (BR); Thiago Vallin Spina, Campinas (BR); Christopher Patrick O'Dowd, Renton, WA (US); Spencer G. Fowers, Duvall, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1071 days.

(21) Appl. No.: 17/889,147

(22) Filed: Aug. 16, 2022

(65) Prior Publication Data

US 2024/0062896 A1 Feb. 22, 2024

(51) Int. Cl.
*G16H 50/20* (2018.01)
*G16H 50/30* (2018.01)

(52) U.S. Cl.
CPC ............. *G16H 50/20* (2018.01); *G16H 50/30* (2018.01)

(58) Field of Classification Search
None
See application file for complete search history.

(56) References Cited

U.S. PATENT DOCUMENTS

2016/0267327 A1* 9/2016 Franz .................. A61B 5/0077
2017/0286618 A1* 10/2017 Abelseth ................ G16H 40/67
2021/0027878 A1* 1/2021 He ......................... G16H 50/70
2022/0261917 A1* 8/2022 Navani .................. G16H 40/67

OTHER PUBLICATIONS

Advances in description of 3D human motion Khokhlova et. at. (Year: 2018).*
Holte, et al., "Human Pose Estimation and Activity Recognition From Multi-View Videos: Comparative Explorations of Recent Developments", In Journal of IEEE Journal of Selected Topics in Signal Processing, vol. 6, Issue 5, Sep. 30, 2012, pp. 538-552.
Khokhlova, et al., "Advances in description of 3D human motion", In Proceedings of Multimedia Tools and Applications, Dec. 2018, pp. 31665-31691.
"International Search Report and Written Opinion Issued in PCT Application No. PCT/US23/027194", Mailed Date: Oct. 20, 2023, 14 Pages.

* cited by examiner

*Primary Examiner* — Mandrita Brahmachari
(74) *Attorney, Agent, or Firm* — Ray Quinney & Nebeker P.C.; James Bullough

(57) ABSTRACT

The present disclosure relates to a four-dimensional (4D) recommendation system for training and implementing a 4D recommendation model to provide health-related recommendation for an individual that is a subject of a volumetric capture performed by a calibrated multi-camera system. In particular, the 4D recommendation system may capture 4D data objects including time-series three-dimensional models and associated annotations and generate a knowledge base including a collection of 4D data objects stored thereon. An input 4D data object may be obtained and compared to the collection of 4D data objects to determine one or more recommendations for the input 4D data object related to the health status of the individual.

18 Claims, 12 Drawing Sheets

TRAINING AND IMPLEMENTING A FOUR-DIMENSIONAL DATA OBJECT RECOMMENDATION MODEL

BACKGROUND

Recent years have seen significant improvements and developments in applications and models that are configured to analyze data and generate outputs. Indeed, as computing applications and various processes become more prevalent and complex, these applications and models are being used for a wide variety of applications and in connection with a wide variety of domains. For example, applications and models (e.g., machine learning models) are being used frequently as tools by medical professionals in providing diagnoses, treatments, and other health-related services.

In addition, as telemedicine has become more popular in recent years, and as healthcare has become more decentralized and specialized, these applications and models are becoming more complex. As more data is being exchanged, and as that data has extended beyond simple text and image content, conventional models and systems for providing diagnoses and treatment tools are becoming outdated and more difficult to apply to a wide variety of use-cases using conventional approaches. Moreover, with multiple providers being located at many remote locations, it is increasingly difficult to combine this data in a meaningful way for a specific patient, a type of diagnoses, or even for patients of variable demographics.

These and other problems exist with regard to developing and implementing software applications and models for providing health-related diagnoses and treatment recommendations.

DETAILED DESCRIPTION

Figure 1:
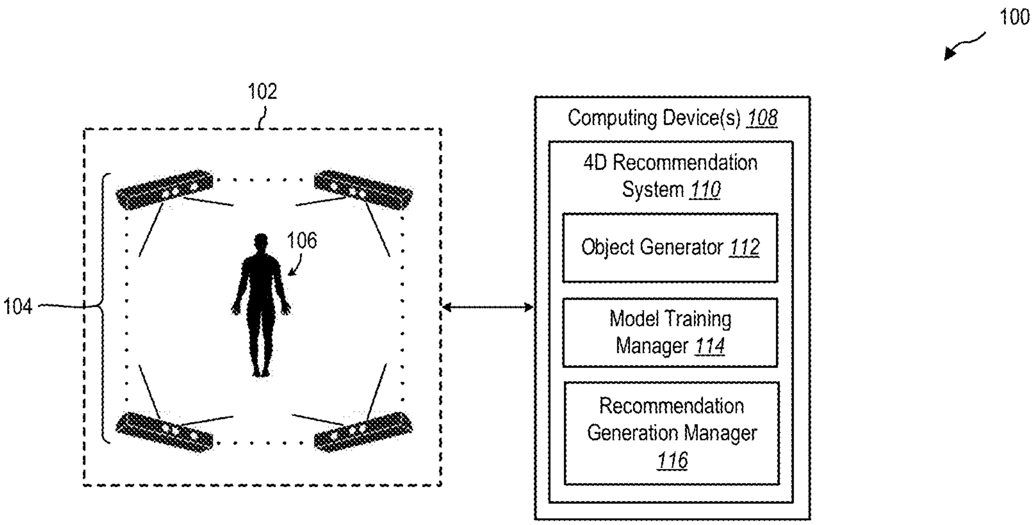
FIG. 1 illustrates an example environment showing a four-dimensional (4D) recommendation system in accordance with one or more embodiments.

The present disclosure relates to a four-dimensional (4D) recommendation system for training and implementing a recommendation model to provide health-related recommendations for an individual that is a subject of a volumetric capture performed by a calibrated multi-camera system. In particular, and as will be discussed in further detail below, the 4D recommendation system may train and implement a 4D recommendation model to generate and provide a recommendation output associated with an input 4D data object that is captured from a multi-camera system.

For example, as will be discussed in further detail below, the 4D recommendation system may train the 4D recommendation model by receiving a plurality of 4D data objects including time-series three-dimensional (3D) models of individuals and associated annotations that are combined within respective 4D data objects. The 4D recommendation system may generate a knowledge base including a collection of 4D data objects. The 4D recommendation system may consider the time-series 3D models and associated annotations and train a 4D recommendation model to output a recommendation (e.g., a health-related recommendation) based on features and other relationships between the 4D data objects of the knowledge base.

As an illustrative example, the 4D recommendation system may receive a plurality of 4D data objects including time-series 3D models captured by multi-camera systems and associated annotations. The 4D recommendation system may additionally generate a knowledge base of the 4D data objects to be compared against by a 4D recommendation model. The 4D recommendation system may further train a 4D recommendation model to output a recommendation output for the 4D data object associated with a target individual. As will be discussed in further detail below, the recommendation output may be generated based on a comparison of a set of features of the 4D data object and features of the plurality of 4D data objects of the knowledge base.

In addition, and as will be discussed in further detail below, the 4D recommendation system may implement the 4D recommendation model in connection with an input 4D object including a time-series 3D model and associated annotations corresponding to a target individual having been scanned by the calibrated multi-camera system. The 4D recommendation system may apply the 4D recommendation model to the input 4D data object to generate a recommendation output in accordance with a training of the 4D recommendation model. This application of the model to the input 4D data object involves identifying features of the input 4D data object, comparing the features to the knowledge base of 4D data objects, and outputting a recommendation based on the comparison of features. The 4D recommendation system may further cause a presentation of the 4D data object to be displayed via a graphical user interface of a client device. It will be understood that, in one or more embodiments described herein, the data included in the 4D data object (e.g., the media content and annotations) will be anonymized to ensure privacy of the individuals associated therewith.

As an illustrative example, the 4D recommendation system may receive an input 4D data object of an individual including a time-series 3D model and associated annotations where the time-series 3D model includes media content captured by a multi-camera system and combined into 3D models showing movement of the individual over a duration of time. The 4D recommendation system may then apply a 4D recommendation model to the input 4D data object to generate a recommendation output for the input 4D data object. The 4D recommendation model may be configured to identify features of a given 4D data object, compare the identified features to features of a knowledge base of 4D data objects to determine a subset of data objects from the knowledge base, and output a recommendation associated with the subset of 4D data objects and based on comparing the various features. The 4D recommendation system may further cause a presentation of the recommendation output to be displayed via a graphical user interface of the client device.

The present disclosure includes a number of practical applications that provide benefits and/or solve problems associated with determining health-related recommendations for an individual based on media content and annotations that are collected in connection with the individual. Some non-limiting examples of these applications are discussed below.

For example, as noted above, the 4D recommendation system considers a 4D data object that is constructed from media content that is simultaneously captured by a multi-camera system. In addition, the 4D data object includes a time-series element in which multiple 3D models are combined into a time-series 3D model that shows movement of an individual over a duration of time. This enables a user (e.g., a healthcare provider, such as a clinician, physician, or other user of the 4D recommendation system) to change a visual perspective as well as view changes of any number of perspectives over a duration of time that the media content is captured. This also provides a perspective of the individual both in real-time (e.g., while the media content is captured) as well as offline (e.g., after the 4D data object is saved and stored).

This unique 4D data object provides a number of benefits in evaluating and providing annotations to the 4D data object. For example, creating a 4D data object that allows a user to view multiple perspectives over a duration of time without being physically present allows multiple collaborators to provide input and other annotations in connection with the 4D data object. As noted above, this additional input can be provided both in real-time (e.g., during a clinical session) and offline (e.g., before or after completion of the clinical session). Further, this decentralized collaboration can be provided in connection with time stamps of the time-series 3D models, thus allowing annotations to be provided in connection with specific durations of time associated with specific media content included within the 4D data object.

By considering 4D data including a combination of 3D media and associated annotations (e.g., text, drawings in the 3D model), the 4D recommendation system can train a recommendation model using fewer instances of training inputs (e.g., 4D data objects) than conventional systems. Indeed, where conventional systems rely primarily on text and/or 2D images, implementations described herein provide information that provide more accurate indications of health-related signals that conventional systems have not considered. This additional, relevant, information eliminates a substantial portion of the guesswork in training the recommendation model(s) thus reducing processing expenses and training time that would otherwise require a significant quantity of training data involved in conventional model training systems.

In one or more embodiments described herein, the 4D recommendation system further refines the recommendation model based additional 4D object models that are captured. For example, where a new patient is scanned (e.g., using a 4D capable multi-camera system), the 4D recommendation system can provide the resulting 4D data object and associated annotations as an additional training dataset to the recommendation model to further refine the algorithms and other features of the recommendation model. In some instances, this may include additional information, such as confirmation of a recommendation, or rejection of a confirmation, which may be used to further inform the model in generating future predictions.

In one or more embodiments described herein, the 4D recommendation system provides a recommendation that enables an individual (e.g., a healthcare provider or a target individual) to facilitate generation of additional detail to include within a 4D data object. Indeed, where relevant 4D data objects from a knowledge base are identified, the 4D recommendation system may determine that additional data would be helpful to provide a more accurate or informed recommendation. For instance, the 4D recommendation system may determine a correlation between an input data object and a subset of data objects from the knowledge base that are similar, but for a specific type of additional data included within the subset of data objects. In some implementations, the 4D recommendation system provides a recommendation to perform a specific gesture or to move in a specific manner to create additional digital media that will provide further context in generating an accurate recommendation. This guidance provides an effective interface that enables an input 4D data object to be refined in a way that increases the likelihood that a recommendation will be accurate or otherwise useful to the individual, particularly in cases where a health care provider is less specialized, or where an individual simply neglects to provide a full set of relevant gestures or movement while being scanned.

As illustrated in the foregoing discussion, the present disclosure utilizes a variety of terms to describe features and advantages of the 4D recommendation system. Additional detail will now be provided regarding the meaning of some of these terms.

For example, as used herein a “4D data object” or simply “4D object” refers to a file, folder, or other data object including 3D media content (e.g., 3D models) and associated annotations that are captured by a multi-camera system over time in accordance with one or more embodiments described herein. The 4D data object may have a variety of formats that enables presentation of a rendering of the 3D media content and associated annotations via a graphical user interface of a client device. The 4D data object may include 3D media that is pieced together into 3D models over a single continuous or multiple discrete durations of time. For instance, a 4D data object may refer to multiple time-series 3D models and associated annotations associated with a specific user. Alternatively, a 4D data object may refer to a single set of 3D models and associated annotations for a user.

As used herein, a “multi-camera system” refers to an arrangement of multiple calibrated camera devices that are oriented to capture media content and depth information of an entity or other object positioned within the field of view of some or all of the multiple camera devices. In one or more embodiments, the multi-camera system includes depth-capable cameras that are oriented around a central point at which an individual may position themselves while the depth-capable camera capture media content over a duration of time. The cameras may be positioned at variable positions around the central point as well as at point angling above or below the central point. The multi-camera system may include any number of depth-capable cameras, with some embodiments ranging from two to ten camera devices. Other implementations may include additional cameras. Further, where one or more embodiments described herein involve different multi-camera systems, some of the different systems may include additional or fewer cameras from one another.

As used herein, a "3D model" refers to digital media captured by multiple cameras from a multi-camera system and pieced together to form a three-dimensional model of an individual or other entity at point within the field of view of the multiple cameras. For example, where a multi-camera system is oriented around a center point, an individual may stand or sit or otherwise position themselves at the center point and the cameras of the multi-camera system may capture video or images of the individual over a duration of time. In this example, the 3D model may refer to the multiple videos or images captured by the respective cameras that are pieced together to provide a 3D-rendering of the individual or other entity positioned at the center point over the duration of time.

As used herein, a "time-series 3D model" refers to multiple 3D models that are combined over a duration of time over which the multi-camera system captured the media content of an individual or other entity. The time-series 3D model may simply include each of multiple 3D models placed in a sequential order associated with a timing of when the corresponding media was captured. In one or more embodiments, the time-series 3D model includes additional renderings to facilitate a smooth transition between the respective renderings of the entity or individual over the duration of time. In one or more embodiments, the time-series 3D model is interactive allowing a user to view any angle of the 3D model at any timestamp from the duration of time over which the individual is represented within the time-series 3D model. As noted above, while a 4D data object may include a single time-series 3D model and associated annotations, in one or more implementations, the 4D data object may include multiple 3D models depicting the same individual captured over different (e.g., non-contiguous) durations of time by the same or different multi-camera systems.

As used herein, an "annotation" or "annotations" refer to text or other content that is tagged, added to, or otherwise associated with a time-series 3D model. In one or more embodiments, an annotation refers to text that is generated by a healthcare provider or other individual observing the time-series 3D model or the individual associated with the time-series 3D model. In one or more embodiments, an annotation may include drawings or other notations added to the time-series 3D model that delimit relevant parts of an individual or other target object of a 4D scan. Annotations may refer to diagnoses, conclusions, or other content associated with a health condition of an individual. Annotations may also refer to demographic data (e.g., sex, age, race, location) of the individual. In one or more embodiments, annotations may refer to other features of the 4D data object, such as status of recovery, which may be text that is explicitly added to the 4D data object or, alternatively, information that is derived after observing a full recovery. In some implementations, annotations refer to other non-text tags that convey information about the 4D data object. For instance, an annotation may associate each 3D model of a knowledge base with a geometric representation of a skeleton or body pose, which can be compared at a time of inference to retrieve a corresponding recommendation. Annotations may be added in real-time (e.g., as the media content is captured) or offline (e.g., at a time after the scan has concluded and the 4D data object is generated). Annotations may be added by any number of users, including multiple health care providers.

As used herein, a "recommendation model" refers to a program, algorithm, or trained model (e.g., a machine learning model) that has been configured to generate or output a recommendation based features and other characteristics of an input 4D data object. In particular, as will be discussed in further detail below, a recommendation model may refer to a trained machine learning model that compares content of a time-series 3D model and associated annotations to corresponding content (e.g., 3D models and annotations) from a knowledge base of 4D models to determine a recommendation associated with the input 4D data object. The 4D recommendation model may refer to a variety of model-types, including (by way of example and not limitation) a machine learning model.

As used herein, a machine learning model may refer to a computer algorithm or model (e.g., a classification model, regression model, a language model, an object detection model) that can be tuned (e.g., trained) based on training input to approximate unknown functions. For example, a machine learning model may refer to a neural network (e.g., a convolutional neural network (CNN), deep neural network (DNN), recurrent neural network (RNN)) or other machine learning algorithm or other machine learning algorithm or architecture that learns and approximates complex functions and generates outputs based on a plurality of inputs provided to the machine learning model. As used herein, the 4D recommendation model may refer to one or multiple models that cooperatively generate one or multiple recommendation outputs based on corresponding inputs. For example, a 4D recommendation model may refer to a system architecture having multiple discrete machine learning components that consider different types of inputs and output different outputs that make up a recommendation associated with an individual.

As used herein, a "recommendation" or "recommendation output" may refer to one or multiple predictions or other outputs associated with media content and associated annotations from a 4D input object provided as input to a recommendation model. The recommendation may specifically be related to a health state of an individual associated with the 4D data object. In one or more embodiments, the recommendation may include multiple predictions associated with the individual, including, but not limited to, a diagnosis, a recommended treatment, a progress prediction, a recovery prediction, and/or an identification of similar 4D objects. In one or more embodiments, a recommendation may include an identification of additional content, such as a gesture or movement to be performed by an individual, which can be captured and added to a 4D data object associated with the individual.

Additional detail in connection with the 4D recommendation system will be discussed in relation to illustrative figures portraying example implementations and showing various features of the 4D recommendation system. FIG. 1 illustrates an example environment 100 showing a multi-camera system 102 in accordance with one or more embodiments. As shown in FIG. 1, the multi-camera system 102 may include a plurality of camera devices 104 positioned around an object 106 (e.g., a centrally positioned individual or other object). Each of the camera devices 104 may be depth-capable cameras that are capable of capturing both visual content and depth information of the object 106. The camera devices 104 may refer to any of a variety of cameras including a range of non-specialized or specialized cameras. For example, the camera devices 104 of the camera system 102 may include mobile devices, motion-sensing input devices (e.g., Kinects), or any other non-specialized device capable of capturing media content and providing the media content to an application that is configured to combine the media content into a 3D model.

As further shown in FIG. 1, the environment 100 includes one or more computing device(s) 108 having the 4D recommendation system 110 implemented thereon. As shown in FIG. 1, the 4D recommendation system 110 may include an object generator 112. The object generator 112 may create a 4D data object based on media content that is collected by the plurality of camera devices 104 of the multi-camera system 102. For example, the object generator 112 may combine images or videos captured from the respective cameras into 3D models that span over a duration of time and which collectively make up a time-series 3D model. This combination of the 3D media content can be performed using any of a variety of image and video combination techniques.

The 3D models may be generated using one of a number of real-time and offline volumetric fusion models for combining content captured from different cameras of a multi-camera system. In one or more implementations, the object generator 112 may use a real-time method that attempts to detect topology changes between an image frame and a surface mesh associated with previously reconstructed frames. In one or more embodiments, the object generator 112 may employ neural networks or other machine learning models for refining obtained results.

In addition to the object generator 112, the 4D recommendation system 110 may include a model training manager 114. The model training manager 114 may provide features and capabilities related to training a recommendation model to output a recommendation associated with a target user based on a 4D data object generated based on a scan performed by the multi-camera system 102. As further shown, the 4D recommendation system 110 may also include a recommendation generation manager 116. The recommendation generation manager 116 may implement the recommendation model to generate a recommendation for an object of interest that has been scanned by the multi-camera system 102. Additional information in connection with the components 112-116 will be discussed in connection with further examples below.

The computing device 108 may refer to various types of computing devices. For example, the computing device 108 may be a mobile device, such as a smartphone, a personal digital assistant (PDA), a tablet, or a laptop. In some implementations, the computing device 108 is a non-mobile devices, such as a desktop computer, server device, or other non-portable computing device. In one or more embodiments, the computing device 108 refers to one or more server nodes on a cloud computing system. Any computing device described herein may include features and functionality described below in connection with FIG. 8.

In addition, as noted above, respective components of the 4D recommendation system 110 may be located across different computing devices. For example, in one or more embodiments, the model training manager 114 is located on a first computing device while the recommendation generation manager 116 is located on a second computing device. These computing devices may be on completely different systems of devices, such as a first device on a local network with a second device being implemented on the cloud. In addition, the object generator 112 may be on any of multiple devices connected or otherwise coupled to a multi-camera system 102. Indeed, in one or more embodiments, the object generator 112 may be implemented as part of the multi-camera system 102 and the 4D data object may be provided as an input to one of the model training manager 114 or recommendation generation manager 116 for further processing.

In addition, while FIG. 1 shows a single multi-camera system 102, this is provided by way of example only as a multi-camera system for scanning training objects (e.g., to be used in generating 4D data objects for training purposes) will often refer to a different system of cameras from a multi-camera system for scanning a target object (e.g., to be used as an input to a trained 4D recommendation model). Moreover, it will be appreciated that different multi-camera systems may include fewer or additional cameras as well as different types of cameras from one another. For example, a first multi-camera system may include ten cameras positioned around a central point while a second multi-camera system may include only two or three cameras positioned around a central point.

Figure 2:
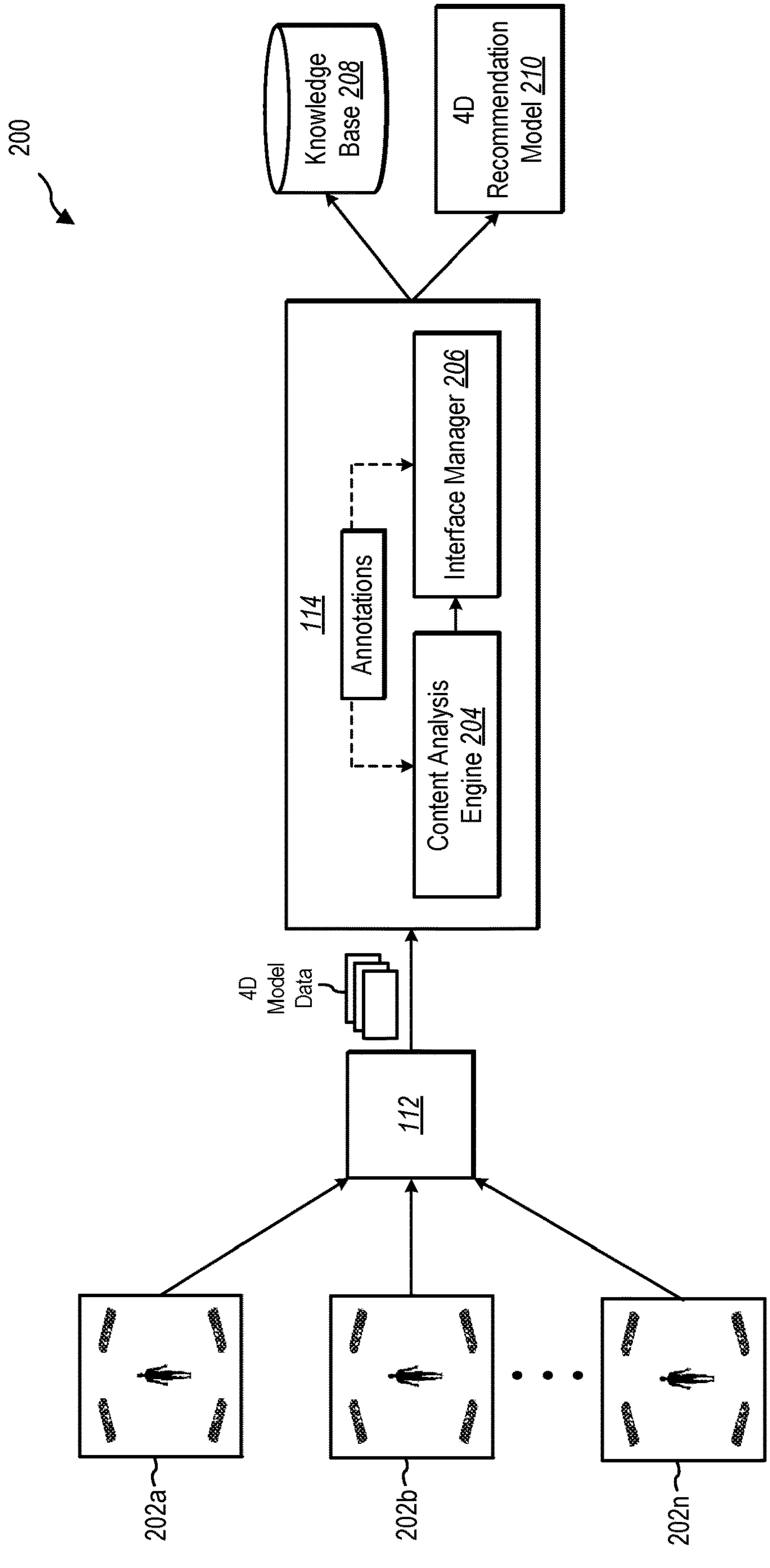
FIG. 2 illustrates an example environment showing a training manager of the 4D recommendation system for generating and training a recommendation model in accordance with one or more embodiments.

FIG. 2 provides additional information in connection with training a 4D recommendation model. In particular, FIG. 2 illustrates components of the 4D recommendation system 110 including the object generator 112 and the model training manager 114 in connection with a workflow 200 that shows an example implementation of a process for training a 4D recommendation model.

As shown in FIG. 2, a plurality of multi-camera systems 202*a-n* may provide media content captured by configurations of camera devices while positioned around a corresponding plurality of objects (e.g., individuals). As shown in the example workflow 200, a first multi-camera system 202*a* may provide media content captured by a first set of camera devices while additional multi-camera systems 202*b-n* may provide media content captured by respective sets of camera devices. Each of the multi-camera systems 202*a-n* can provide media content in connection with any number of scanned objects. In addition, while some of the multi-camera systems 202*a-n* may include similar numbers and arrangements of camera devices, one or more of the multi-camera systems 202*a-n* may have fewer or additional camera devices from one another. Indeed, as mentioned above, the multi-camera systems 202*a-n* may include two or more camera devices that are capable of capturing media content and depth information of an object.

As shown in FIG. 2, each of the multi-camera systems 202*a-n* can provide media content to the object generator 112. As discussed above, the object generator 112 may generate time-series 3D models of a plurality of objects scanned by respective multi-camera systems 202*a-n*. In one or more embodiments, the time-series 3D models represent a portion of the 4D object data (e.g., the media portion). As shown in FIG. 2, the object generator 112 can provide the 4D model data (e.g., the time-series 3D models) to the recommendation generation manager 116 for further processing.

As shown in FIG. 2, the recommendation generation manager 116 may include a content analysis engine 204 and an interface manager 206. The content analysis engine 204 may analyze any portion of the 4D model data to identify or otherwise determine features associated with respective 4D data objects. In particular, the content analysis engine 204 may include one or more models for identifying visual features of an image or 3D model, such as an object that is depicted within the media, a gesture that is performed by an individual, or other detectable feature of the 4D data object. In one or more embodiments, the content analysis engine 204 involves a program or software that identifies features of the 4D data object. Alternatively, in one or more embodiments, a physician or other health provider indicates features of the media content while carrying out a clinical session. In one or more embodiments, these features are included as annotations in conjunction with the 3D model(s) within the 4D data object.

As just mentioned above, and as shown in FIG. 2, the recommendation generation manager 116 may include an interface manager 206. The interface manager 206 may provide an interactive interface that enables a user (e.g., a clinician, physician, or other health provider) of a computing device to provide annotations in connection with the media portion of the 4D data object. For example, prior to or after scanning the individual, a user may provide patient data (e.g., demographic data, such as age and gender) as well as any text that provides additional information about the individual. This patient data may be provided independent from the content included within the 4D data object, and may be provided by the patient themselves or from a medical or examination history of the individual.

In addition to demographic and other patient data, the user may add additional text via an interface of a computing device. This may include observations made in real-time while performing the scan and during a clinical session. This may additionally include text added to the 4D data object offline (e.g., after a clinical session is done and based on a future observation of the time-series 3D model(s). Additional information in connection with adding annotations to a 4D data object will be discussed in connection with various examples below.

After constructing the 4D data object including both the time-series 3D model(s) and the associated annotations, copies of the 4D data object may be stored in a knowledge base 208. As mentioned above, the knowledge base 208 may refer to a storage of 4D data objects that are accessible to a 4D recommendation model 210. For example, as will be discussed in further detail below, the knowledge base 208 may include a collection of 4D data objects that are accessible to the 4D recommendation model 210 for the purpose of comparing an input 4D data object to the collection of 4D data objects to determine a recommendation including a prediction about a health state of an individual associated with the input 4D data object.

In addition to providing the 4D data objects for storage in the knowledge base 208, the 4D recommendation system 110 may cause the 4D recommendation model 210 to be trained to predict any number of recommendations for a given 4D data object. For example, the 4D recommendation model 210 may be trained to output a predicted diagnosis, a predicted recovery status, a predicted recovery timeline, or any other recommendation associated with the given 4D data object. As noted above, a recommendation may include any number of predictions associated with content of the 4D data object.

In one or more embodiments, the 4D recommendation model 210 is trained based on a set of 4D data objects and associated recommendations, which may refer to specific recommendations or recommendations included within the annotations. In one or more embodiments, the training of the 4D recommendation model 210 may be unsupervised where the model is trained to predict an output based on the training dataset and data included therein. Other implementations may involve a supervised training of the model where a user provides a ground truth recommendation output corresponding to the type of recommendation that the 4D recommendation model 210 is trained to emulate. In either example, the 4D recommendation model 210 may include multiple models that are each trained to generate different types of outputs. Moreover, as will be discussed below, a user may provide one or more parameters that indicate what type of recommendation to output, which may involve indicating which model of multiple machine learning models the 4D recommendation model 210 should user in producing a recommendation output.

Figure 3:
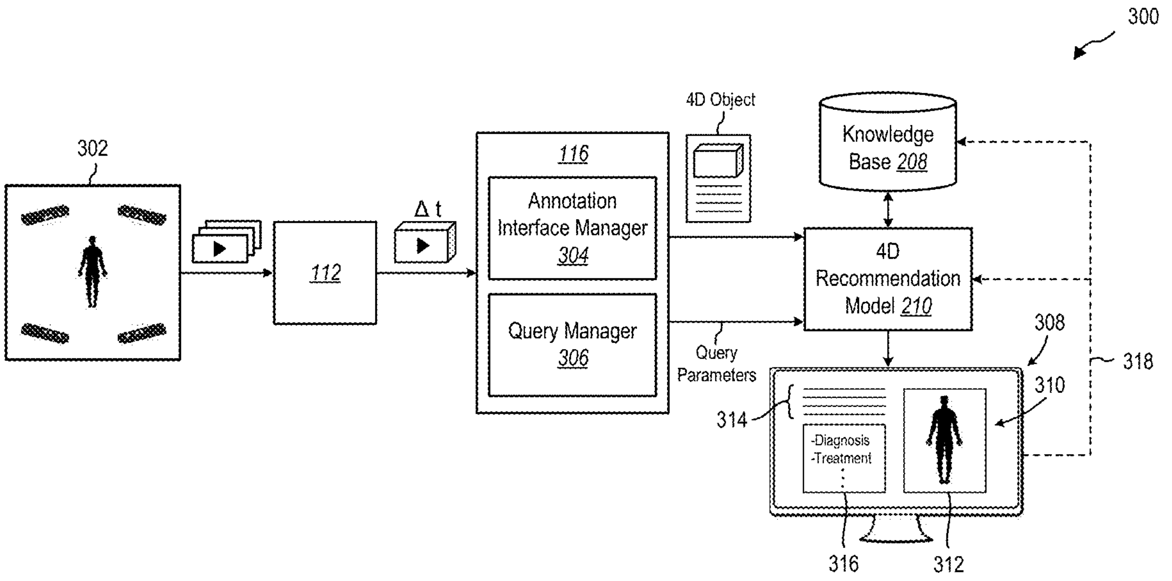
FIG. 3 illustrates an example environment showing an example implementation of the recommendation model in accordance with one or more embodiments.

In addition to training the 4D recommendation model 210 to provide a recommendation output for a given 4D data object, the 4D recommendation system 110 may further implement a trained 4D recommendation model 210 in connection with an input 4D object associated with a target individual (or other target object). FIG. 3 provides an example implementation of a workflow 300 showing an implementation of a trained 4D recommendation model 210 in accordance with one or more embodiments.

For example, as shown in FIG. 3, the example workflow 300 shows a multi-camera system 302 that is capable of scanning a target individual located at a central position between a plurality of depth-capable cameras. The multi-camera system 302 may include similar features as other multi-camera systems 302 described herein. Indeed, in one or more embodiments, the multi-camera system 302 may be the same system as used in providing some or all of the media content used to train the 4D recommendation model 210. Similar to other implementations described above, the multi-camera system 302 may provide the media content to an object generator 112 to piece together content captured by the respective cameras into a time-series 3D model. As shown in FIG. 3, the object generator 112 may output a time-series 3D model based on content captured by the plurality of cameras.

As shown in FIG. 3, the recommendation generation manager 116 may receive the time-series 3D model and add annotations to the model as part of the process of generating an input 4D data object. As shown in FIG. 3, the recommendation generation manager 116 may include an annotation interface manager 304. The annotation interface manager 304 may provide an interface (e.g., via a graphical user interface of a client device) that enables a user to add text or other non-media content to a 4D data object including the time-series 3D model. For example, the annotation interface manager 304 may provide an opportunity to associate each of multiple 3D models with a geometric representation of a skeleton or body pose. This comparison enables the recommendation generation manager 116 to compare the content of the 3D model(s) with the geometric representation at a time of inference and retrieve a corresponding recommendation. In addition, in one or more implementations, the annotation interface manager 304 may facilitate adding text to the 4D data object in a similar manner as discussed above in connection with FIG. 2.

Similar to one or more embodiments described herein, the annotation interface manager 304 may provide an interface before or after performing the scan of the target individual. For example, in one or more embodiments, the annotation interface manager 304 provides an interface that enables a clinician, physician, or other health provider to add patient data to the resulting 4D data object.

In addition to providing an interface to add data before the scan, the annotation interface manager 304 may provide an interface that enables text to be added to the 4D data object during or after the scan. For example, a user may add general comments about a health condition of an individual. The user may add comments about the clinical session, such as notes about how a user moves or comments about particular gestures. In one or more embodiments, the user may add diagnoses, recommended treatments, progress reports, or any other information about the condition of an individual that is the subject of the scan.

In addition to generally adding annotations to the 4D data object, the annotation interface manager 304 may enable a user to add or otherwise associate the annotations to specific time ranges of the time-series 3D data object. For example, a user may add an annotation to a specific timestamp of the time-series 3D model. Indeed, the user may add any number of annotations to any number of timestamps (or across different ranges of timestamps) across a duration of time associated with the time-series 3D data object.

As further shown in FIG. 3, the recommendation generation manager 116 includes a query manager 306. Once the 4D data object is generated, the query manager 306 may receive one or more query parameters or other general input indicating parameters that the 4D recommendation model 210 should consider in determining a recommendation output for the input 4D data object. For example, the query manager 306 may receive an input of a particular demographic (e.g., age range, a gender identifier) that the 4D recommendation model 210 can use to narrow a search of data objects within the knowledge base 208 to compare against the features of the input 4D data object. In addition, or as an alternative to patient data, the query manager 306 may receive an identification of a particular health condition or type of injury of interest for the target individual that the 4D recommendation model 210 may similarly use in narrowing a search of 4D data objects in the knowledge base to compare against.

As shown in FIG. 3, the 4D data object and the query parameters may be provided as inputs to the 4D recommendation model 210. Upon receiving these inputs, the 4D recommendation model 210 may determine features of the 4D data object based on training of the 4D recommendation model 210 and/or any models within the 4D recommendation model 210 that have been trained to identify particular features. This may include evaluating the media content of the time-series 3D model to identify particular gestures or movements or any other detectable features associated with movement of the target individual. In one or more embodiments, this analysis is guided by the query parameters provided, such as a parameter indicating a specific type of injury, a particular demographic of individuals, or other input parameter that may limit a comparison of the input 4D data object to a subset of 4D objects stored in the knowledge base 208. In some implementations, the query parameters may determine one or more specific machine learning models of the 4D recommendation model 210 that may be applied to the input 4D data object.

As shown in FIG. 3, the 4D recommendation model 210 may perform a comparison of the input 4D data object to the knowledge base 208 to determine a recommendation output. As noted above, the 4D recommendation model 210 may compare identified features of the input 4D data object to features of the 4D data objects from the knowledge base 208. This may involve comparing similar types of media content (e.g., media portions of the 4D data objects), such as similar movements, similar gestures, media content that has been tagged with similar injury identifiers, etc. In one or more embodiments, the 4D recommendation model 210 may additionally compare text of the 4D data objects. For example, the 4D recommendation model 210 may determine similarities between terms, phrases, diagnoses, treatments, geometric annotations, or any other of the annotations between the input 4D data object and the 4D data objects stored in the knowledge base 208.

In one or more embodiments, the 4D recommendation model 210 may perform a comparison of the features as mapped in a multi-dimensional space representative of the set of features. For example, upon identifying features of the 4D data objects, the 4D recommendation model 210 may compare respective mappings of the 4D data objects to determine a subset of 4D data objects that are mapped to a location in the multi-dimensional space to determine which of the collection of 4D data objects from the knowledge base 208 are within a threshold distance (e.g., having a threshold metric of similarity) of the input 4D data object. Based on this comparison (or other metric of similarity), the 4D recommendation model 210 may determine a specific subset of 4D data objects that are likely to be comparable to the input 4D data object and which will likely have similar recommendations associated therewith.

Similar principles in comparing features may apply to comparison of geometric annotations. For example, in one or more embodiments, geometric annotations may be used to detect anomalies in movement of an individual. These geometric annotations may be added by a user observing the scan or based on training of a model that is configured to identify various anomalies. Thus, in addition to other example features and comparisons of data types discussed herein, 4D data objects having similar geometric annotations (e.g., similar detected anomalies in movement) may also be retrieved for comparing features with an input 4D data object. These geometric features between similar 4D data objects may be compared in determining a recommendation based on the geometric annotations.

Upon performing this comparison, the 4D recommendation model 210 may output a recommendation including a prediction related to a health state of the target individual associated with the input 4D data object. Generating the recommendation may be based on a consensus of those 4D data objects within the identified subset of data objects having a threshold similarity with the input 4D data object.

As shown in FIG. 3, the 4D recommendation model 210 may provide the recommendation output to a computing device 308 having a graphical user interface 310 thereon for providing a presentation of the recommendation output. In this example, the graphical user interface 310 provides a presentation of the recommendation output including (by way of example), an object display 312 showing a rendering of the time-series 3D model, the annotations 314 added by one or more users involved in performing the scan of the target individual or evaluating the input 4D data object offline, and one or more recommendations 316 associated with the target individual. In this example, the recommendations 316 may include a diagnosis and a treatment, though additional recommendations may be provided within the presentation.

As shown in FIG. 3, the recommendation and any additional notes provided by a healthcare provider may be used in further training the 4D recommendation model 210 and/or updating the knowledge base. As shown in FIG. 3, the computing device 308 may provide additional annotations 318 added to the 4D data object based on the recommendations provided. For example, a physician may indicate some measure of confidence that the predicted diagnosis is right, or may provide additional notes based on further evaluation or understanding of the target individual. In one or more embodiments, a user may disagree with the recommendation or determine that the recommendation is flawed and provide this information to the 4D recommendation model 210 for further consideration in tuning one or more algorithms of the 4D recommendation model 210.

Figure 4A:
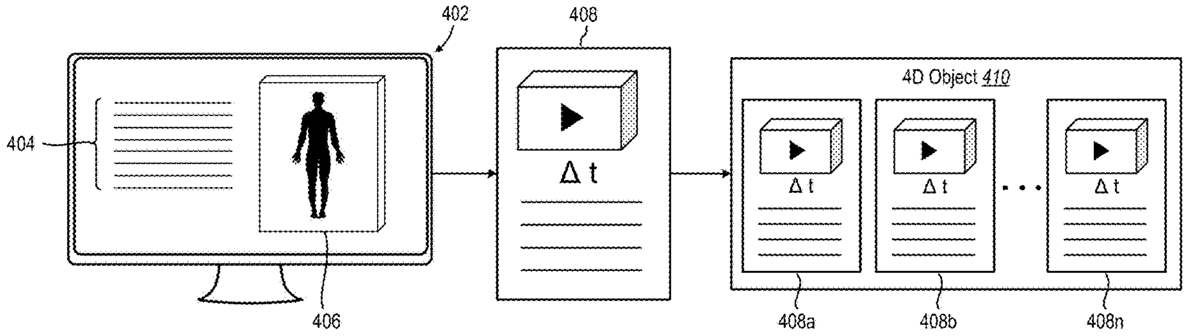
FIGS. 4A-4C illustrate example features associated with training the recommendation model in accordance with one or more embodiments.
Figure 4B:
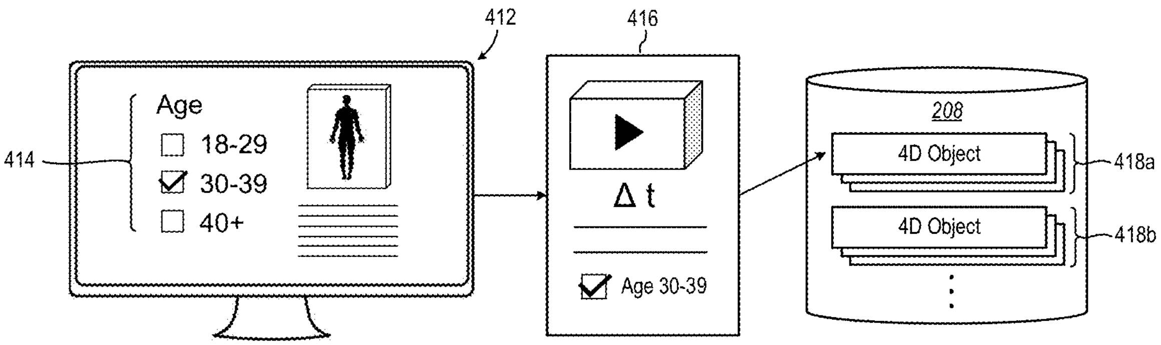
Figure 4C:
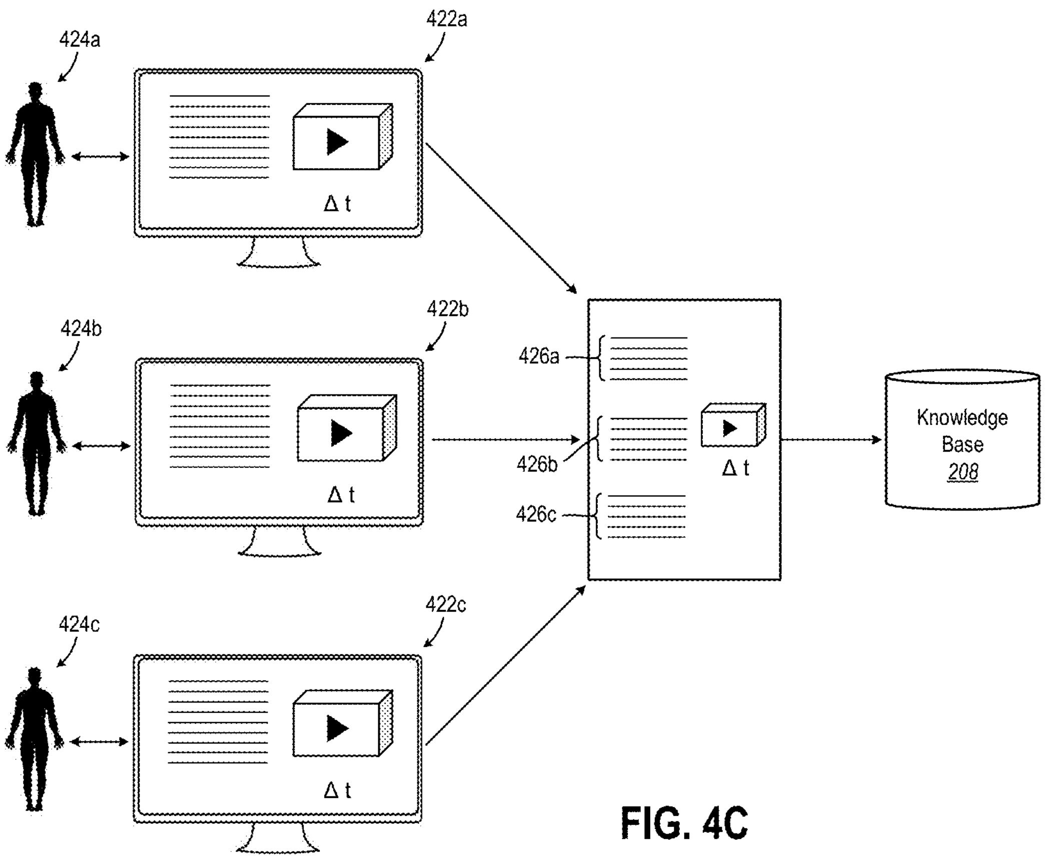
Figure 5A:
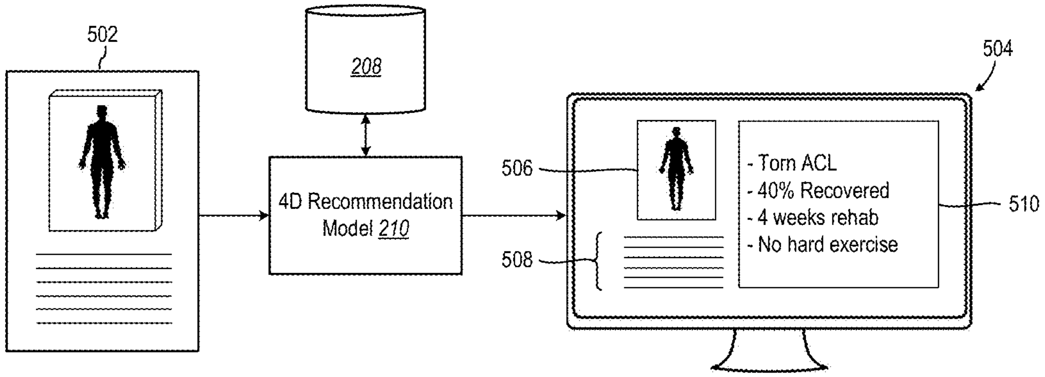
FIGS. 5A-5C illustrate example features associated with implementing the recommendation model in accordance with one or more embodiments.
Figure 5B:
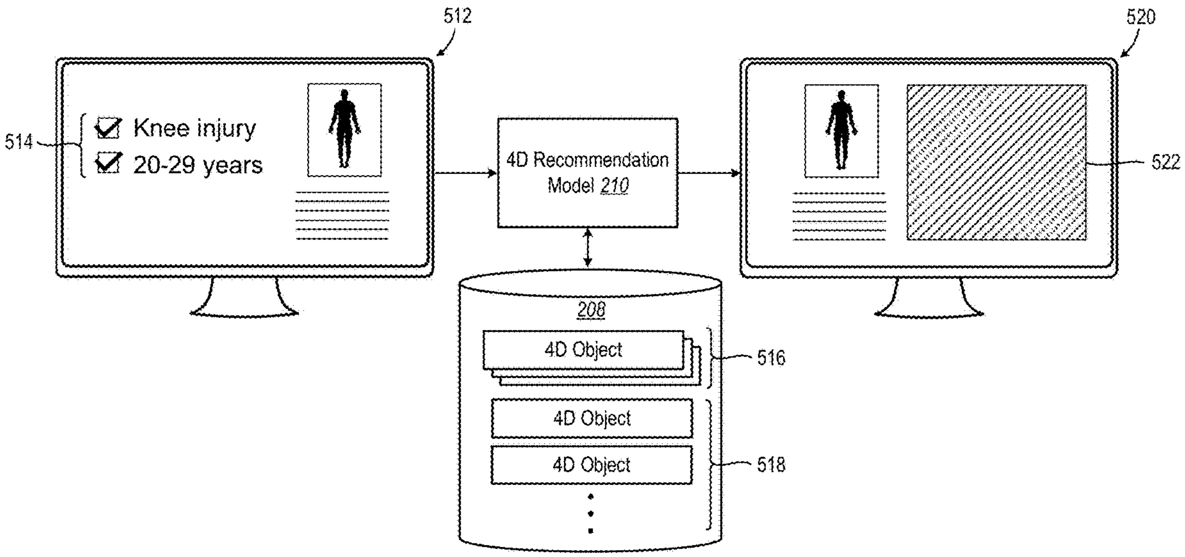
Figure 5C:
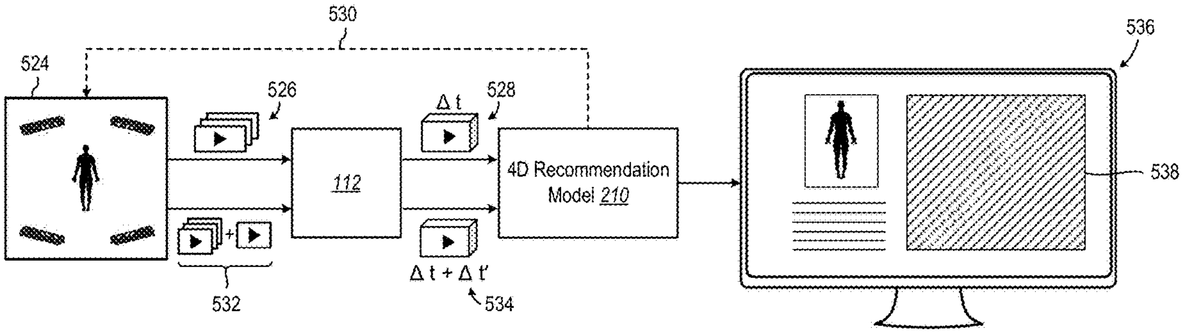

Additional detail will now be given in connection with various examples associated with training and/or implementing a 4D recommendation model in accordance with one or more embodiments. For example, FIGS. 4A-4C illustrate example features and functionality of the 4D recommendation system 110 in connection with training a 4D recommendation model. In addition, FIGS. 5A-5C illustrate example features and functionality of the 4D recommendation system 110 in connection with implementing the trained 4D recommendation model and generating recommendation for display via a graphical user interface of the computing device. It will be appreciated that features described in connection with each of these figures may apply to one or more of the embodiments described herein, even where those features are described in different figures or in connection with different example implementations.

FIG. 4A illustrates an example implementation showing an addition of a time-series 3D model and associated annotations into a 4D data object that includes multiple associated 3D models and annotations. For example, as shown in FIG. 4A, a computing device 402 may present a 4D data object including both annotations 404 added by a user of the computing device 402 and a rendering of the time-series 3D model 406 associated with the annotations 404. In one or more embodiments, a user of the computing device 402 may interact with the display of the time-series 3D model to zoom in and/or view different angles of the scanned object over a specific duration of time. This may involve interacting with the display of the 3D model at a specific timestamp to change an angle or perspective and then selecting a timestamp within the duration of time to view the specific angle.

As shown in FIG. 4A, the computing device 402 may provide the resulting 4D data object instance 408 to be included within a 4D object 410 including any number of 4D object instances 408*a-n* associated with the same individual and/or health condition. In this example, the 4D object 410 may include any number of 4D object instances 408*a-n* associated with the same individual and/or corresponding to a particular health condition. For instance, where a user injures an arm, the 4D object 410 may include 4D object instances 408*a-n* spanning over a long period of time showing recovery of the individual over time. These groupings of 4D object instances may be stored in the knowledge base to provide additional context in comparing features of an input 4D data object to corresponding sets of 4D object instances. This can be particularly helpful where a recommendation indicates a recovery state, such as an estimated percentage an injury is recovered, an estimated timeline of recovery, or other recommendation that could be derived from a comparison to a grouping of 4D object instances that span over some period of time.

FIG. 4B provides another example feature of the 4D recommendation system 110 in connection with training a 4D recommendation model. For example, as shown in FIG. 4B, a computing device 412 may include an interface showing a listing of feature options 414. In this example, the interface provides a listing of age ranges that a user may select in associating a 4D data object with a corresponding age demographic of an individual. By checking the "30-39 age range," the user may tag the 4D data object with an age-range tag that associates the 4D data object with other 4D data objects of a similar age range.

As shown in FIG. 4B, the 4D recommendation system 110 may add the tagged 4D data object 416 to the knowledge base 208. As shown in FIG. 4B, the tagged 4D data object 416 may be associated with a first set of 4D objects 418*a* within the knowledge base associated with similar age ranges. The knowledge base 208 may additionally include a second set of 4D objects 418*b* associated with a different range of ages. Indeed, the knowledge base 208 may include any number of groupings of 4D objects associated with different features or other classifiers. These groupings or clusters of 4D objects may be stored together or may simply be tagged with the indicated feature and retrieved using conventional query processing techniques when analyzing or otherwise processing an input 4D data object.

FIG. 4C provides another example feature of the 4D recommendation system 110 in connection with training a 4D recommendation model and creating the knowledge base 208. As noted above, the 4D recommendation system 110 enables addition of annotations at any point in the lifecycle of the 4D data objects. For example, annotations may be added prior to performing a scan of an individual by a multi-camera system. Annotations may also be added during a scan or after the scan.

This flexibility in adding the annotations to the 4D data objects in combination with the ability to view different angles of the time-series 3D data object over the specific duration of time enables users to view or add annotations at any point in time after performing the scan. As shown in FIG. 4C, multiple users 424*a-c* may be involved in adding annotations to a 4D data object. In this example, each of the multiple users interact with respective computing devices 422*a-c* to add annotations to the same 4D data object.

More specifically, a first user 424*a* may interact with a first computing device 422*a* to add a first set of annotations 426*a* to a 4D data object. Meanwhile, at the same or different time, a second user 424*b* may interact with a second computing device 422*b* to add a second set of annotations 426*b* to the 4D data object. As further shown, a third user 424*c* may interact with a third computing device 422*c* to add a third set of annotations 426*c* to the 4D data object. Similar to implementations discussed above, these annotations may be added to specific timestamps or be associated with the time-series 3D model generally.

As shown in FIG. 4C, the annotated 4D data object may be added to the knowledge base 208. Once stored, the annotated 4D data object may be accessible by any number of users for a variety of purposes. For example, other health providers may review the 4D data object for research or other purposes. In one or more embodiments described herein, features of the annotated 4D data object may be compared against features of an input 4D data object to determine similarities and ultimately output a recommendation for a target individual based on a comparison of the features of the different 4D data objects.

As noted above, FIGS. 5A-5C illustrate example features of the 4D recommendation system 110 in connection with implementing a trained 4D recommendation model to determine a recommendation for an input 4D data object. For example, FIG. 5A illustrates an example application of a 4D recommendation model 210 to an input data object to generate an example set of recommendations.

As shown in FIG. 5A, an input 4D data object 502 is provided as input to a 4D recommendation model 210. Similar to one or more embodiments described herein, the 4D data object 502 may include any similar features as other 4D data objects described herein. In addition, the 4D recommendation model 210 may refer to one or multiple machine learning models that are trained to generate a recommendation output based on a given 4D data object. While not shown in FIG. 5A, the 4D recommendation model 210 may additionally receive one or more query parameters indicating further details about a target individual associated with the input 4D data object 502, such as demographic information, an identification of an injury, or any other information that is relevant to the target individual.

Upon receiving the input 4D data object and any additional inputs, the 4D recommendation model 210 may access 4D data objects from a knowledge base 208 to compare against features of the input 4D data object 502. For example, the 4D recommendation model 210 may identify features of the attribute portion of media portion of the input 4D data object 502 to compare against features of the 4D data objects from the knowledge base 208. In accordance with one or more embodiments described above (and below), the 4D recommendation model 210 may output any recommendation for which the 4D recommendation model 210 has been trained to generate. In one or more embodiments, the 4D recommendation model 210 may include multiple machine learning models that have been trained to produce different types of recommendations based on identified similarities between the input 4D data object and data objects from the knowledge base 208 and/or based on parameters of a received query in conjunction with the input 4D data object 502.

As shown in FIG. 5A, the 4D recommendation model 210 may provide an output recommendation and cause a computing device 504 to provide a presentation of the recommendation(s). As shown in FIG. 5A, a presentation of the recommendation output may include a rendering of the time-series 3D model 506 and any portion of the associated annotations 508. The presentation may also include a recommendation display 510.

As shown in FIG. 5A, the recommendation display 510 may include any number of recommendations output by the 4D recommendation model 210. In this example, the recommendation display 510 may include a listing of recommendations, such as a diagnosis or identification of an injury type (e.g., "torn ACL"), an identified state of recovery from the injury (e.g., "40% recovered"), an estimated recovery time and/or recommended treatment (e.g., "4 weeks rehab," "No hard exercise"). In accordance with one or more embodiments described herein, the recommendations may be generated based on the comparison of the input 4D data object 502 and the 4D data objects from the knowledge base 208. Moreover, the recommendation display 510 may include any number of recommendations associated with a variety of health conditions.

FIG. 5B illustrates an example implementation of the 4D recommendation model 210 in connection with limiting a scope of comparison between the input 4D data object and a subset of 4D objects from the knowledge base 208. For example, as shown in FIG. 5B, a user of a computing device 512 may indicate a number of query parameters by selecting one or more options associated with different features of the input 4D data object. In the illustrated example, a user of the computing device 512 may select one of a plurality of interactive icons 514 associated with different individual characteristics. For example, a user of the computing device 512 may select a first option indicating that the target individual has suffered a knee injury and that the individual is between 20-29 years old.

Upon receiving the input 4D data object and the selected query parameters, the 4D recommendation model 210 may compare the 4D data object with 4D data objects from the knowledge base 208. In this example, the 4D recommendation model 210 may consider a first subset of 4D objects 516 that are tagged with metadata or other identifiers indicating that subjects associated with the first subset of 4D objects 516 suffered knee injuries and were 20-29 years old. In this example, the 4D recommendation model 210 may limit comparing the features of the input 4D data object with only those 4D objects from the first subset of 4D objects 516 while disregarding comparisons with features from additional 4D data objects 518 from the knowledge base 208.

This selective comparison between 4D data objects is beneficial for a number of reasons. For example, by selectively comparing the input 4D data object with only a first subset of 4D objects 516 rather than all 4D objects within the knowledge base 208, the 4D recommendation model 210 may more accurately determine relevant recommendations for a target individual with or without human supervision. In addition, by selectively identifying the first subset of 4D objects 516, the 4D recommendation model 210 is able to perform the comparison of features using fewer processing resources and provide the recommendation(s) faster than a system in which the input 4D data object is compared against a larger collection of 4D data objects. Thus, the 4D recommendation model 210 is able to provide more accurate recommendations while using fewer processing resources than conventional systems.

As shown in FIG. 5B, the 4D recommendation model 210 may provide the recommendation out to a computing device 520 for providing a display of the recommendation thereon. In the example shown in FIG. 5B, the computing device 520 provides a presentation of the recommendation including a display of a time-series 3D model, annotations associated with the time-series 3D model, and a recommendation display 522 showing one or more recommendations associated with the input 4D data object.

Moving on, FIG. 5C illustrates an example implementation of the 4D recommendation model 210 in connection with requesting additional information from an individual associated with an input 4D data object. For example, as shown in FIG. 5C, a multi-camera system 524 may be used to capture media content of an individual positioned within fields of view of multiple camera devices that make up the multi-camera system 524. In accordance with one or more embodiments, captured media content 526 is provided to an object generator 112 to create a time-series 3D model based on the content captured by the multi-camera system 524.

The object generator 112 may provide an input 4D data object 528 including the time-series 3D model data and the annotation data as an input to the 4D recommendation model 210. Based on a comparison of the input 4D data object 528 to 4D data objects from a knowledge base, the recommendation model 210 may determine that additional information is needed to determine an accurate recommendation. For example, based on a comparison of the input 4D data object 528 to the knowledge base, the 4D recommendation model 210 may determine that 4D data objects of a similar type of injury include a series of gestures or movements detected therein that is not included within the media content portion of the 4D data objects 528.

In this example, the 4D recommendation model 210 may identify one or more gestures or other movements that may be performed by a target individual and provide movement instructions 530 to an operator of the multi-camera system 524. These movement instructions 530 may indicate a series of movements or an identification of one or more gestures to be performed by an individual and captured by the multi-camera system 524.

Upon capturing additional media content including a depiction of the additional movements or gestures, the multi-camera system 524 can provide updated media content 532 to the object generator 112 for further processing. As shown in FIG. 5C, the object generator 112 may generate an updated 4D data object 534 (e.g., an updated version of the input 4D data object) including a combination of the originally captured media content and the newly captured media content to provide as an input to the 4D recommendation model 210.

As shown in FIG. 5C, the 4D recommendation model 210 may compare the updated 4D data object 534 with a knowledge base of 4D data objects and determine a recommendation for the updated 4D data object 534. As shown in FIG. 5C, the 4D recommendation model 210 may provide the recommendation to a computing device 536 and cause the computing device 536 to provide a presentation of the recommendation via a graphical user interface of the computing device 536. In the example shown, the presentation of the recommendation includes a rendering of the time-series 3D model, associated annotations, and a recommendation display 538 showing one or more recommendations in accordance with one or more embodiments described herein.

While not shown in FIGS. 5A-5C, the presentation of the recommendation output may include additional features not explicitly illustrated in these figures. For example, in one or more embodiments, the 4D recommendation system may provide a display of one or more 4D data objects from the knowledge base that are determined to be similar to the input 4D data object. In this example, a user of a computing device can view similar 4D data objects including media and associated annotations to further understand the similarities between the features of the input 4D data object and the similar 4D data objects from the knowledge base. This would enable a user to view the time-series 3D data objects of similar diagnoses or recommendations side-by-side to confirm similarities or identify differences between the different subjects, thus further informing the health care provider as to the accuracy (or inaccuracy) of the recommendations.

Figure 6:
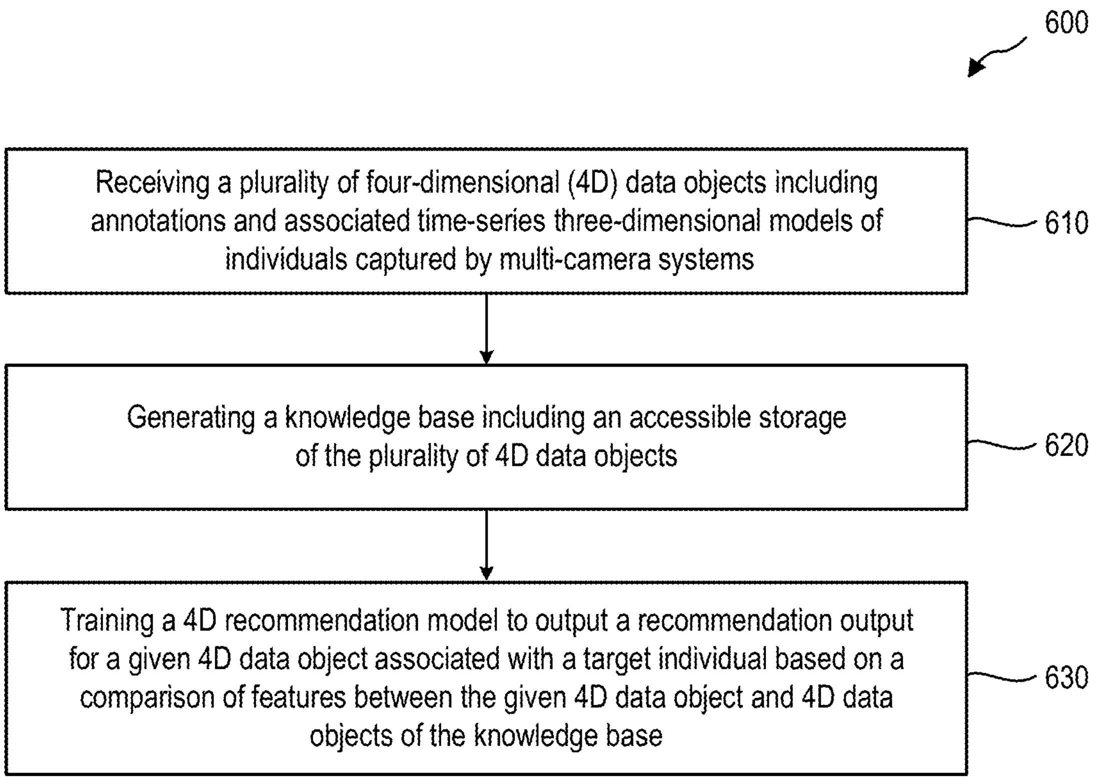
FIG. 6 illustrates an example series of acts of training a recommendation model in accordance with one or more embodiments.
Figure 7:
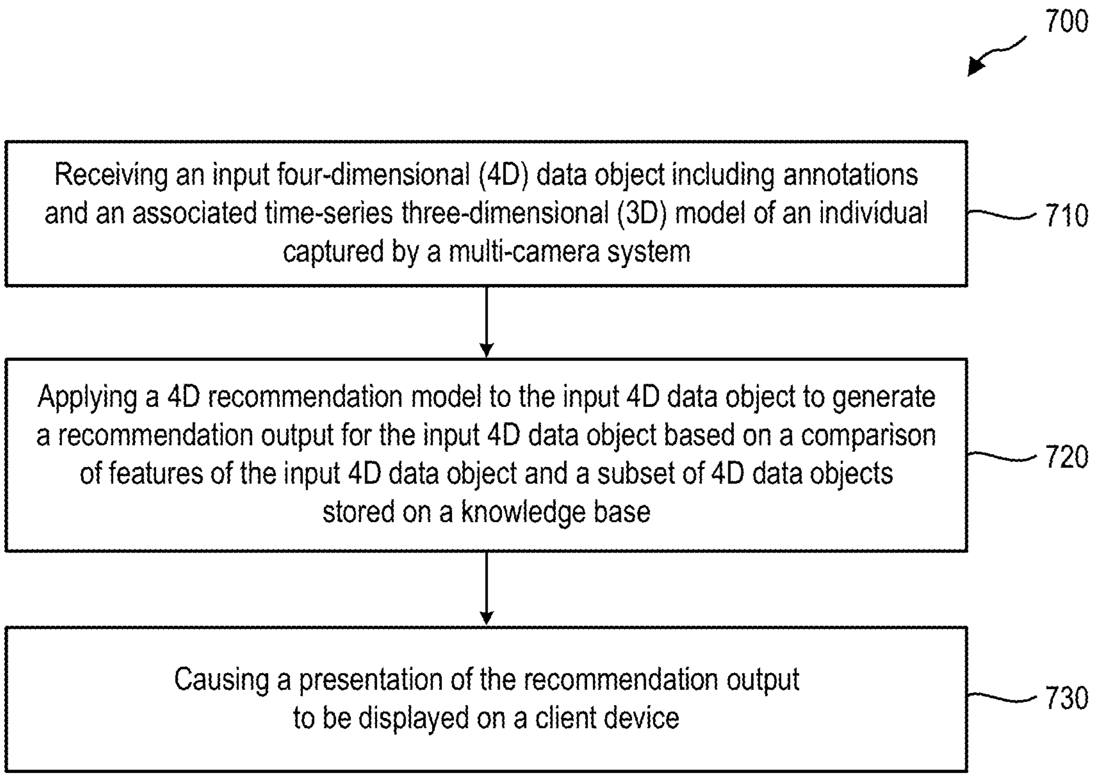
FIG. 7 illustrates an example series of acts of implementing a trained recommendation model in accordance with one or more embodiments.

Turning now to FIGS. 6-7, these figures illustrate example flowcharts including series of acts for training and implementing a 4D recommendation model in connection with determining recommendations for an individual associated with a 4D data object captured by a multi-camera system. While FIGS. 6-7 illustrate acts according to one or more embodiments, alternative embodiments may omit, add to, reorder, and/or modify any of the acts shown in FIGS. 6-7. The acts of FIGS. 6-7 can be performed as part of a method. Alternatively, a non-transitory computer-readable medium can include instructions that, when executed by one or more processors, cause a computing device to perform the acts of FIGS. 6-7. In still further embodiments, a system can perform the acts of FIGS. 6-7.

FIG. 6 shows an example series of acts 600 related to generating a knowledge base of 4D data objects and training a 4D recommendation model in accordance with one or more embodiments described herein. As shown in FIG. 6, the series of acts 600 includes an act 610 of receiving a plurality of four-dimensional (4D) data objects including annotations and associated time-series three-dimensional (3D) models of individuals captured by multi-camera systems. In one or more embodiments, the act 610 involves receiving a plurality of four-dimensional (4D) data objects, the plurality of 4D data objects including time-series three-dimensional (3D) models of individuals and annotations associated with the time-series 3D models, each time-series 3D model from the plurality of 4D objects including media content captured by a multi-camera system and combined into 3D models showing movement of an individual over a duration of time. In one or more embodiments, the multi-camera system includes plurality of depth capable cameras oriented around a central position and calibrated to capture media content depicting the individual over the duration of time.

As further shown in FIG. 6, the series of acts 600 includes an act 620 of generating a knowledge base including an accessible storage of the plurality of 4D data objects. In one or more embodiments, the act 620 includes generating a knowledge base of the plurality of 4D data objects, the knowledge base including an accessible storage of the plurality of 4D data objects.

As further shown in FIG. 6, the series of acts 600 includes an act 630 of training a 4D recommendation model to output a recommendation output for a given 4D data object associated with a target individual based on a comparison of features between the given 4D data object and 4D data objects of the knowledge base. In one or more embodiments, the act 630 includes training a 4D recommendation model to output a recommendation output for a 4D data object associated with a target individual, the recommendation output being generated based on a comparison of a first set of features of the 4D data object and features of the plurality of 4D data objects from the knowledge base.

In one or more embodiments, the annotations associated with the time-series 3D models include text associated with individuals depicted by the time-series 3D models. In one or more embodiments, the annotations associated with the time-series 3D models include demographic data associated with the individuals. In one or more embodiments, the annotations associated with the time-series 3D models include human-generated recommendations determined by a healthcare provider and included within one of the plurality of 4D data objects. In one or more embodiments, the annotations associated with the time-series 3D models include geometric annotations and/or drawings of the body (or portion of the body) of an individual.

In one or more embodiments, the recommendation output includes a predicted recommendation for the target individual based on similarities between features of the 4D data object and a subset of 4D data objects from the plurality of 4D data objects having a shared set of features as the 4D data object. In one or more embodiments, the recommendation output includes a predicted diagnosis of a health condition of the target individual based on the comparison of the first set of features and features of the plurality of 4D data objects. In one or more embodiments, the recommendation output includes a predicted recovery status of a health condition based on the comparison of the first set of features and features of the plurality of 4D data objects.

In one or more embodiments, the recommendation output includes an identification of a gesture to be performed by the target individual to collect additional information to include within the 4D data object. Further, in one or more embodiments, the comparison of features includes a comparison of features from the plurality of 4D data objects of the knowledge base and additional media content captured and included within the 4D data object based on performance of the gesture by the target individual.

FIG. 7 illustrates an example series of acts 700 related to implementing a 4D recommendation model in connection with an input 4D data object to determine and present a recommendation for the input data object. As shown in FIG. 7, the series of acts 700 includes an act 710 of receiving an input 4D data object including annotations and an associated time-series 3D model of an individual captured by a multi-camera system. In one or more embodiments, the act 710 includes receiving an input four-dimensional (4D) data object including a time-series three-dimensional (3D) model of an individual and annotations associated with the individual, the time-series 3D model including media content captured by a multi-camera system and combined into 3D models showing movement of the individual over a duration of time.

As further shown in FIG. 7, the series of acts 700 includes an act 720 of applying a 4D recommendation model to the input 4D data object to generate a recommendation output for the input 4D data object based on a comparison of features of the input 4D data object and a subset of 4D data objects stored on a knowledge base. In one or more embodiments, the act 720 includes applying the 4D recommendation model to the input 4D data object to generate a recommendation output for the input 4D data object where the 4D recommendation model is configured to identify features of a given 4D data object, compare the identified features to features of a knowledge base of 4D data objects to determine a subset of 4D data objects from the knowledge base having a threshold similarity to the given 4D data object, and output a recommendation associated with the subset of 4D data objects and based on comparing the identifiers features to features of 4D data objects from the knowledge base, the recommendation including a prediction associated with the given 4D data object.

As further shown in FIG. 7, the series of acts 700 includes an act 730 of causing a presentation of the recommendation output to be displayed on a client device. In one or more embodiments, the act 730 includes causing a presentation of the recommendation output to be displayed via a graphical user interface of a client device.

In one or more embodiments, the threshold similarity includes a threshold number of shared features between the subset of 4D data objects and the identified features of the given 4D data object. In one or more embodiments, the threshold similarity includes a threshold similarity between text from annotations of the given 4D data object and text of annotations from the subset of 4D data objects. In one or more embodiments, the threshold similarity includes a threshold number of similar demographic features between the given 4D data object and individuals associated with the subset of 4D data objects.

In one or more embodiments, the threshold similarity includes a threshold similarity between geometric annotations. For instance, where geometric annotations are used to detect anomalies in movement of an individual, 4D data objects having similar geometric annotations (e.g., similar detected anomalies in movement) may be retrieved for comparing features with an input 4D data object and determining a recommendation based on the geometric annotations.

In one or more embodiments, the series of acts 700 include an act of receiving a user input identifying a subset of features of the input 4D data object, wherein the recommendation output is determined based on a comparison between the input 4D data object and a subset of 4D data objects from the knowledge base that share the identified subset of features.

In one or more embodiments, the series of acts 700 includes an act of providing, via the graphical user interface of the client device, an identification of a gesture to be performed by the individual to collect additional information to include within an updated version of the input 4D data object. The series of acts 700 may additionally include applying the 4D recommendation model to the updated version of the input 4D data object to generate the recommendation output for the updated version of the input 4D data object, the recommendation output being based on the additional information included within the input 4D data object.

In one or more embodiments, the recommendation output includes a predicted diagnosis of a health condition of the individual. The recommendation output may additionally, or alternatively, include a predicted recovery status of a health condition of the individual.

Figure 8:
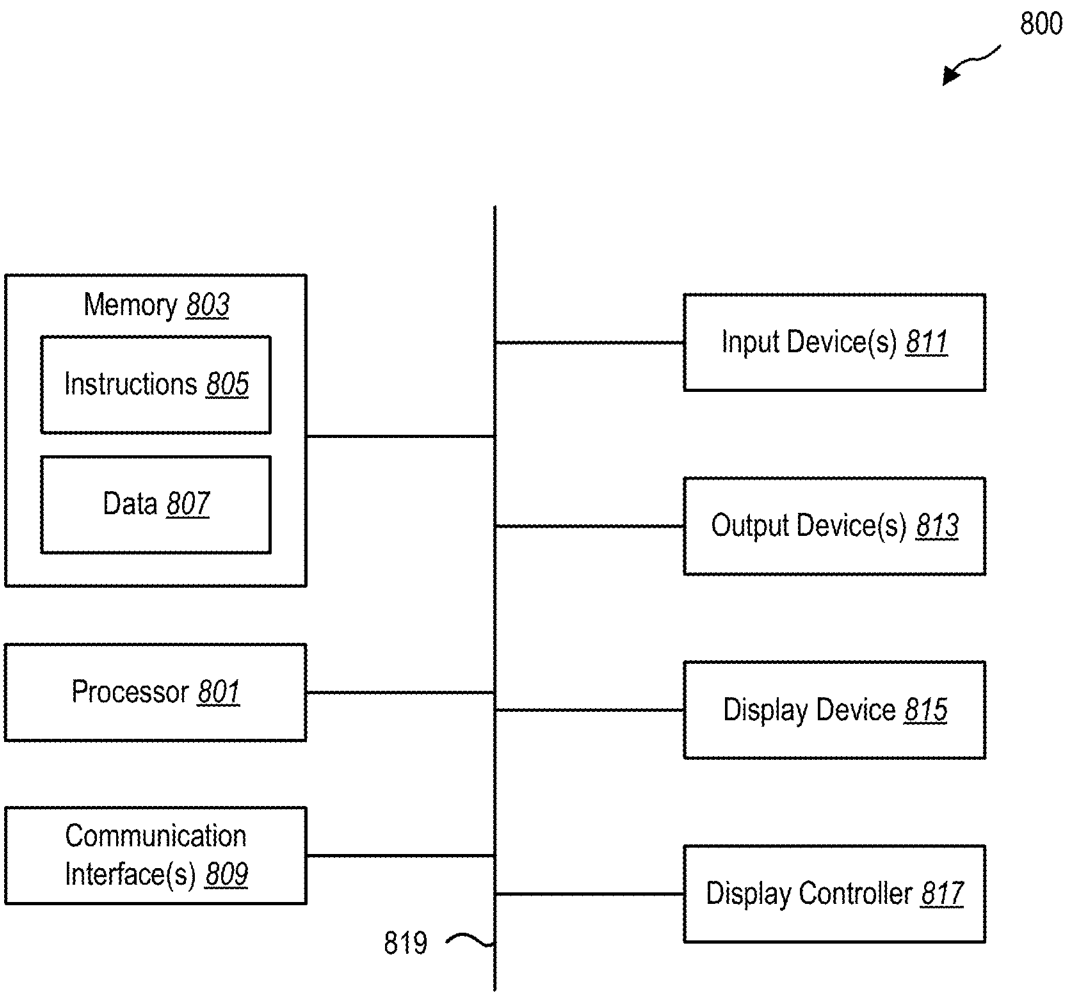
FIG. 8 illustrates certain components that may be included within a computer system.

FIG. 8 illustrates certain components that may be included within a computer system 800. One or more computer systems 800 may be used to implement the various devices, components, and systems described herein.

The computer system 800 includes a processor 801. The processor 801 may be a general purpose single- or multi-chip microprocessor (e.g., an Advanced RISC (Reduced Instruction Set Computer) Machine (ARM)), a special-purpose microprocessor (e.g., a digital signal processor (DSP)), a microcontroller, a programmable gate array, etc. The processor 801 may be referred to as a central processing unit (CPU). Although just a single processor 801 is shown in the computer system 800 of FIG. 8, in an alternative configuration, a combination of processors (e.g., an ARM and DSP) could be used.

The computer system 800 also includes memory 803 in electronic communication with the processor 801. The memory 803 may be any electronic component capable of storing electronic information. For example, the memory 803 may be embodied as random access memory (RAM), read-only memory (ROM), magnetic disk storage media, optical storage media, flash memory devices in RAM, on-board memory included with the processor, erasable programmable read-only memory (EPROM), electrically erasable programmable read-only memory (EEPROM) memory, registers, and so forth, including combinations thereof.

Instructions 805 and data 807 may be stored in the memory 803. The instructions 805 may be executable by the processor 801 to implement some or all of the functionality disclosed herein. Executing the instructions 805 may involve the use of the data 807 that is stored in the memory 803. Any of the various examples of modules and components described herein may be implemented, partially or wholly, as instructions 805 stored in memory 803 and executed by the processor 801. Any of the various examples of data described herein may be among the data 807 that is stored in memory 803 and used during execution of the instructions 805 by the processor 801.

A computer system 800 may also include one or more communication interfaces 809 for communicating with other electronic devices. The communication interface(s) 809 may be based on wired communication technology, wireless communication technology, or both. Some examples of communication interfaces 809 include a Universal Serial Bus (USB), an Ethernet adapter, a wireless adapter that operates in accordance with an Institute of Electrical and Electronics Engineers (IEEE) 802.11 wireless communication protocol, a Bluetooth® wireless communication adapter, and an infrared (IR) communication port.

A computer system 800 may also include one or more input devices 811 and one or more output devices 813. Some examples of input devices 811 include a keyboard, mouse, microphone, remote control device, button, joystick, trackball, touchpad, and lightpen. Some examples of output devices 813 include a speaker and a printer. One specific type of output device that is typically included in a computer system 800 is a display device 815. Display devices 815 used with embodiments disclosed herein may utilize any suitable image projection technology, such as liquid crystal display (LCD), light-emitting diode (LED), gas plasma, electroluminescence, or the like. A display controller 817 may also be provided, for converting data 807 stored in the memory 803 into text, graphics, and/or moving images (as appropriate) shown on the display device 815.

The various components of the computer system 800 may be coupled together by one or more buses, which may include a power bus, a control signal bus, a status signal bus, a data bus, etc. For the sake of clarity, the various buses are illustrated in FIG. 8 as a bus system 819.

The techniques described herein may be implemented in hardware, software, firmware, or any combination thereof, unless specifically described as being implemented in a specific manner. Any features described as modules, components, or the like may also be implemented together in an integrated logic device or separately as discrete but interoperable logic devices. If implemented in software, the techniques may be realized at least in part by a non-transitory processor-readable storage medium comprising instructions that, when executed by at least one processor, perform one or more of the methods described herein. The instructions may be organized into routines, programs, objects, components, data structures, etc., which may perform particular tasks and/or implement particular datatypes, and which may be combined or distributed as desired in various embodiments.

The steps and/or actions of the methods described herein may be interchanged with one another without departing from the scope of the claims. In other words, unless a specific order of steps or actions is required for proper operation of the method that is being described, the order and/or use of specific steps and/or actions may be modified without departing from the scope of the claims.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element or feature described in relation to an embodiment herein may be combinable with any element or feature of any other embodiment described herein, where compatible.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method, comprising:

receiving a plurality of four-dimensional (4D) data objects, the plurality of 4D data objects including time-series three-dimensional (3D) models of individuals and annotations associated with the time-series 3D models, each time-series 3D model from the plurality of 4D objects including media content captured by a multi-camera system and combined into 3D models showing movement of an individual over a duration of time;

generating a knowledge base of the plurality of 4D data objects, the knowledge base including an accessible storage of the plurality of 4D data objects; and training a 4D recommendation model to;

identify features of a given 4D data object;

compare the identified features to features of the knowledge base of the plurality of 4D data objects to determine a subset of 4D data objects from the knowledge base having a threshold similarity to the given 4D data object;

compare the given 4D data object to the subset of 4D data objects from the knowledge base to determine that one or more features are missing from the given 4D data object; and generate an output including a recommendation associated with the subset of 4D data objects and based on determining that the one or more features are missing from the given 4D data object, the recommendation including a gesture to perform by a given individual such that capturing additional media content while the given individual performs the gesture would capture the one or more features that are missing from the given 4D data object.

2. The method of claim 1, wherein the annotations associated with the time-series 3D models include text associated with individuals depicted by the time-series 3D models.

3. The method of claim 1, wherein the annotations associated with the time-series 3D models include demographic data associated with the individuals.

4. The method of claim 1, wherein the annotations associated with the time-series 3D models include human-generated recommendations determined by a healthcare provider and included within one of the plurality of 4D data objects.

5. The method of claim 1, wherein the output includes a predicted recommendation for the target individual based on similarities between features of the given 4D data object and the subset of 4D data objects from the plurality of 4D data objects having a shared set of features as the given 4D data object.

6. The method of claim 1, wherein the output includes a predicted diagnosis of a health condition of the target individual based on the comparison of the first set of features and features of the plurality of 4D data objects.

7. The method of claim 1, wherein the recommendation output includes a predicted recovery status of a health condition based on the comparison of the features of the given data object and features of the plurality of 4D data objects.

8. The method of claim 1, wherein the multi-camera system includes plurality of depth capable cameras oriented around a central position and calibrated to capture media content depicting the individual over the duration of time.

9. A method, comprising:

receiving an input four-dimensional (4D) data object including a time-series three-dimensional (3D) model of an individual and annotations associated with the individual, the time-series 3D model including media content captured by a multi-camera system and combined into 3D models showing movement of the individual over a duration of time;

applying a 4D recommendation model to the input 4D data object to generate a recommendation output for the input 4D data object, the 4D recommendation model being configured to:

identify features of a given 4D data object;

compare the identified features to features of a knowledge base of 4D data objects to determine a subset of 4D data objects from the knowledge base having a threshold similarity to the given 4D data object;

compare the given 4D data object to the subset of 4D data objects from the knowledge base to determine that one or more features are missing from the given 4D data object; and generate an output including a recommendation associated with the subset of 4D data objects and based on determining that the one or more features are missing from the given 4D data object, the recommendation including a gesture to perform by a given individual such that capturing additional media content while the given individual performs the gesture would capture the one or more features that are missing within the given 4D data object; and causing a presentation of the recommendation output to be displayed via a graphical user interface of a client device, prompting the individual to perform the gesture while the multi-camera system captures additional media content to update the 4D data object.

10. The method of claim 9, wherein the threshold similarity includes a threshold number of shared features between the subset of 4D data objects and the identified features of the given 4D data object.

11. The method of claim 9, wherein the threshold similarity includes a threshold similarity between text from annotations of the given 4D data object and text of annotations from the subset of 4D data objects.

12. The method of claim 9, wherein the threshold similarity includes a threshold number of similar demographic features between the given 4D data object and individuals associated with the subset of 4D data objects.

13. The method of claim 9, further comprising receiving a user input identifying a subset of features of the input 4D data object, wherein the recommendation output is determined based on a comparison between the input 4D data object and a subset of 4D data objects from the knowledge base that share the identified subset of features.

14. The method of claim 9, further comprising providing, via the graphical user interface of the client device, an identification of a gesture to be performed by the individual to collect additional information to include within an updated version of the input 4D data object.

15. The method of claim 14, further comprising applying the 4D recommendation model to the updated version of the input 4D data object to generate the recommendation output for the updated version of the input 4D data object, the recommendation output being based on the additional information included within the input 4D data object.

16. The method of claim 9, wherein the recommendation output includes one or more of:

a predicted diagnosis of a health condition of the individual; or a predicted recovery status of a health condition of the individual.

17. A system, comprising:

at least one processor;

memory in electronic communication with the at least one processor; and instructions stored in the memory, the instructions being executable by the at least one processor to:

receiving a plurality of four-dimensional (4D) data objects, the plurality of 4D data objects including time-series three-dimensional (3D) models of individuals and annotations associated with the time-series 3D models, each time-series 3D model from the plurality of 4D objects including media content captured by a multi-camera system and combined into 3D models showing movement of an individual over a duration of time;

generating a knowledge base of the plurality of 4D data objects, the knowledge base including an accessible storage of the plurality of 4D data objects; and training a 4D recommendation model to:

identify features of a given 4D data object;

compare the identified features to features of the knowledge base of the plurality of 4D data objects to determine a subset of 4D data objects from the knowledge base having a threshold similarity to the given 4D data object;

compare the given 4D data object to the subset of 4D data objects from the knowledge base to determine that one or more features are missing from the given 4D data object; and generate an output including a recommendation associated with the subset of 4D data objects and based on determining that the one or more features are missing from the given 4D data object, the recommendation including a gesture to perform by a given individual such that capturing additional media content while the given individual performs the gesture would capture the one or more features that are missing from the given 4D data object.

18. The system of claim 17, wherein the output includes a predicted recommendation for the target individual based on similarities between features of the given 4D data object and the subset of 4D data objects from the plurality of 4D data objects having a shared set of features as the given 4D data object.

* * * * *